United States Patent [19]

Selvin et al.

[11] Patent Number: 5,109,452
[45] Date of Patent: Apr. 28, 1992

[54] ELECTRICAL-OPTICAL HYBRID CONNECTOR

[75] Inventors: Gerald J. Selvin, Huntington Beach; Leslie M. Borsuk, Los Alamitos, both of Calif.

[73] Assignee: Puritan-Bennett Corporation, Carlsbad, Calif.

[21] Appl. No.: 553,998

[22] Filed: Jul. 16, 1990

[51] Int. Cl.$^5$ .............................. G02B 6/36
[52] U.S. Cl. ........................ 385/69; 385/56; 385/60
[58] Field of Search ............. 350/96.20, 96.21

[56] References Cited

U.S. PATENT DOCUMENTS

| | | | |
|---|---|---|---|
| 4,303,301 | 12/1981 | Teichert et al. | 350/96.18 |
| 4,508,416 | 4/1985 | Oftedahl | 339/176 M |
| 4,597,631 | 7/1986 | Flores | 350/96.20 |
| 4,645,295 | 2/1987 | Pronovost | 350/96.20 |
| 4,657,333 | 4/1987 | Anderson | 339/164 R |
| 4,678,264 | 7/1987 | Bowen et al. | 350/96.20 |
| 4,721,358 | 1/1988 | Faber et al. | 350/96.21 |
| 4,762,388 | 8/1988 | Tanaka et al. | 350/96.20 |
| 4,767,168 | 8/1988 | Grandy | 350/96.2 |
| 4,767,181 | 8/1988 | McEowen | 350/96.21 |
| 4,801,191 | 1/1989 | Nakai et al. | 350/96.20 |

Primary Examiner—John D. Lee
Assistant Examiner—Phan T. Heartney
Attorney, Agent, or Firm—Fulwider Patton Lee & Utecht

[57] ABSTRACT

A hybrid electrical optical connector employing a push-pull plug receptacle combination. A hood structure protruding from the plug component of the connector simultaneously serves to ensure that the plug is properly rotationally oriented with respect to the receptacle prior to insertion, that the individual terminals are guided toward the respective terminal receiving channels, and that the plug is latched in place once fully engaged. A rigid armature allows the plug to be partially assembled and tested prior to final overmolding. In its final overmolded form the plug is impervious to the influx of contamination and can withstand a substantial amount of physical abuse. The inexpensive materials used in the construction of the plug and the ease of assembly yield a low cost plug well suited for use in conjunction with a disposable peripheral device.

7 Claims, 2 Drawing Sheets

ELECTRICAL-OPTICAL HYBRID CONNECTOR

BACKGROUND OF THE INVENTION

1. Field of the Invention

The present invention relates to connectors and more particularly pertains to connectors for the simultaneous coupling of electrical and optical conduits.

2. Background of the Prior Art

A multitude of devices are disclosed in the prior art that serve to interconnect electrical conductors as well as optic fibers in a single hybrid connector. Combining two such dissimilar interconnecting functions poses special problems as the requirements for making good electrical contact differ from what is involved in achieving a good optical coupling. For example, in order to achieve a good electrical interconnection, it is generally desirable that the contacting surfaces engage in a sweeping motion to clear away any contamination or oxidation that may have accumulated. Once engaged, substantial force is required in order to maintain electrical contact. The optical coupling of two light conducting fibers on the other hand requires extremely precise axial alignment of the respective fiber ends. A lateral offset of just a few microns or an angular misalignment of a few minutes of arc can significantly compromise the transmission of light energy. The connectors in which both the described requirements for the electrical connection and the precision required for the optical connection are simultaneously achieved typically result in devices that are rather large, complex, difficult to manufacture and expensive, especially when designed for use under harsh conditions. Additionally, such devices can be difficult to manipulate, a problem that is compounding when the connectors are used under adverse circumstances. The expense inherent in the prior art connectors is especially limiting when a connector is intended for use in conjunction with an expendable or disposable peripheral device.

SUMMARY OF THE INVENTION

The present invention seeks to overcome the prior art's inherent disadvantages with the push-pull type electrical-optical hybrid connector described in detail herein below. More particularly, the invention provides a connector that is ideally suited for interconnecting an expendable or disposable peripheral device with permanent, expensive equipment and one that is additionally capable of surviving the conditions the peripheral device is typically subjected to. An example of an application for which the connector of the present invention is ideally suited is medical instrumentation which employs a single-use probe electrically and optically interconnected to analyzing equipment. Contamination concerns not only preclude the probe's reuse, but also requires it to initially undergo sterilization. The harsh conditions of sterilization and the potential misuse or abuse such a device may be subjected to when handled by lay-personnel or by personnel under adverse conditions requires, a connector associated therewith to be tough, and easy to use in addition to satisfying the economic considerations associated with its intended disposability.

The connector of the present invention provides a receptacle and plug arrangement wherein the minimization of cost and maximization of the ability to withstand abuse is concentrated in the plug component which is to be permanently affixed to the peripheral device. All of the moving parts, relatively delicate elements, and high-precision surfaces necessary to achieve a proper electrical and optical coupling are accommodated in the receptacle while the plug consists of relatively few, sturdy, and easily assembled components constructed of relatively inexpensive materials. As a result, the plug can easily withstand high impact loads, thermal loads, is impervious to harsh chemicals and can be produced at minimal cost.

The plug component serves to positively locate a plurality of electrical and optical terminals in a preselected protruding arrangement for receipt within the respective receiving channels of the receptacle. A hood surrounds the arrangement of protruding terminals and extends substantially beyond their ends to prevent inadvertent contact therewith. Besides protecting the terminals from damage, the hood is formed such that its interior surface engages a structure within the receptacle to guide the terminals toward the receiving orifices during engagement. The hood's exterior surface is contoured to key the plug's rotational orientation to that of the receptacle and additionally serves to latch the plug into position within the receptacle once fully engaged.

Additional features that serve to minimize the cost of the plug are inherent in the construction and assembly of its components. A single molded structure integrates the above-described hood with an armature which eases the initial arrangement of the terminals in the preselected orientation, enables the terminals so oriented to be locked in place, firmly grasps the cable carrying the electrical and optical conduits, serves to properly route the conduits to their respective terminals, facilitates the attachment of the electrical wires to the terminals, and permits the function of the plug to be fully tested prior to the completion of the assembly process. When deemed functional or once any identified fault has been rectified, the entire armature is overmolded with an elastomer that bonds to the armature as well as the cable's jacket. Apertures in the armature's structure promote the flow of overmolding in and around the entire structure's surfaces while ridges therein further serve to provide a good mechanical interlock between the armature and overmolding.

Other features and advantages of the present invention will become apparent from the following detailed description, taken in conjunction with the accompanying drawings, which illustrate by way of example, the principles of the invention.

DETAILED DESCRIPTION OF THE PREFERRED EMBODIMENT

Figure 1:
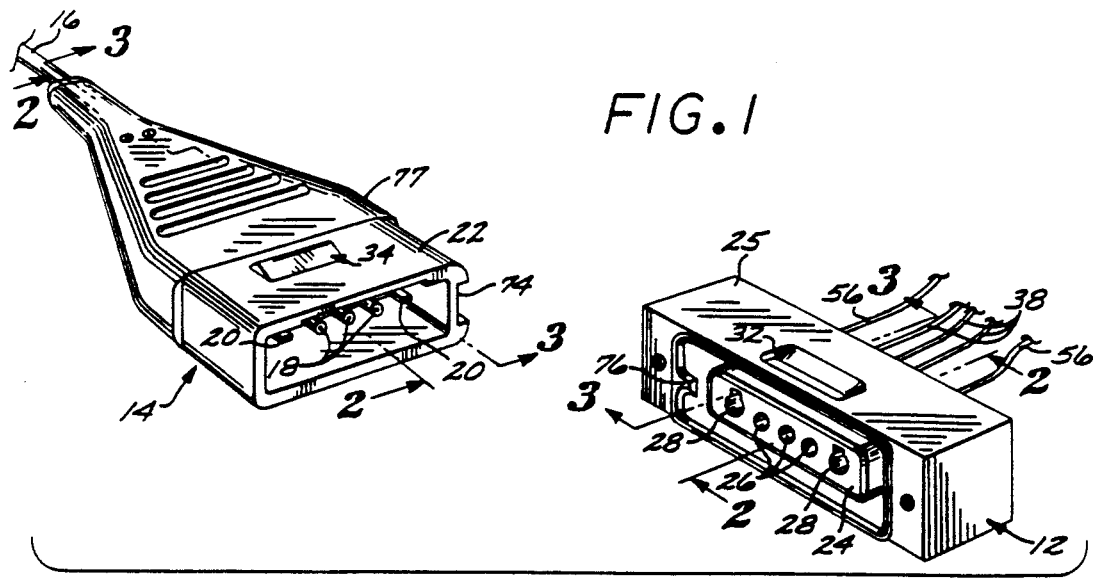
FIG. 1 is a perspective view showing the connector receptacle and connector plug of the present invention.

The figures illustrate a preferred embodiment of the connector according to the present invention. The connector serves to interconnect electrical and optical conduits with a push-pull receptacle/plug combination. FIG. 1 illustrates the receptacle 12 and plug 14 in an uncoupled state. Ideally the receptacle 12 would be directly affixed to an instrument (not shown) or a cable leading directly thereto while the plug 14 would be attached to a disposable peripheral device (not shown) such as a probe or a sensor.

The cable 16 associated with plug 14 carries a plurality of optical and electrical conduits therein, the ends of which are attached to or operatively integrated within terminals 18, 20, a portion of which protrudes from within the interior of plug 14. A hood 22 extends around and substantially out beyond the individual terminals 18, 20 as shown in FIG. 1. The receptacle 12 incorporates therein a terminal receiving mound 24 that extends outwardly from within the receptacle body 25. The terminal receiving mound 24 has an array of terminal receiving channels 26, 28 therein. The receiving channels 26, 28 are arranged and dimensioned to receive into their interiors the protruding portions of terminals 18, 20 of plug 14. Each channel accommodates in its interior an optical 29 or electrical terminal 51 capable of functionally coupling with the plug's corresponding optical and electrical terminal. Optical and electrical conduits 38, 56 are subsequently routed therefrom to the instrument with which receptacle 12 is associated.

The fiber optic terminals 18, 29 employed in the connector of the present invention are of conventional design. Briefly, each terminal is of cylindrical symmetry and carries an optic fiber 37, 38 along its central axis. Each fiber terminates in an optically flat surface 40, 42 that coincides with the end face of the terminal. Terminal 29 has a sleeve 45 extending therefrom dimensioned to accommodate the end portion of terminal 18 therein and prevent relative axial movement of the two terminals 18, 29 once in close proximity to one another. It is a connector's function to enable two fiber ends within respective terminals to be brought into axial alignment with one another and to then maintain the terminals, end faces and the fibers' optical surfaces, so aligned, in firm contact with one another.

Figure 2:
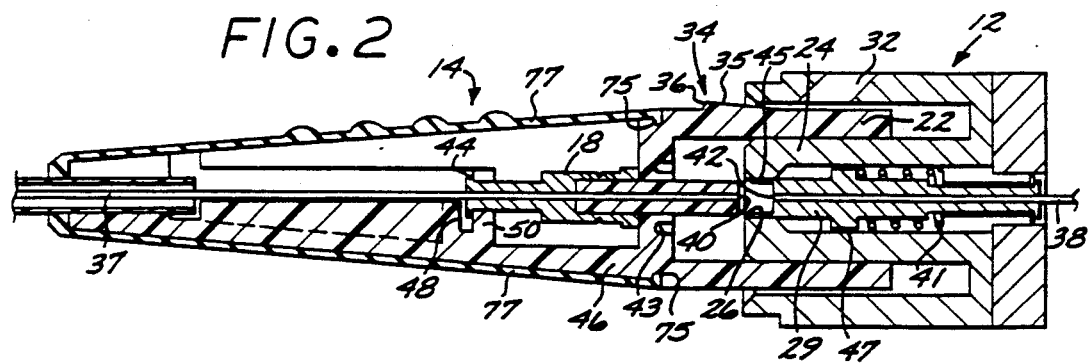
FIG. 2 is an enlarged, cross-sectional view taken along lines 2—2 of FIG. 1.

FIG. 2 is a cross-sectional view of plug 14 and receptacle 12 in a partially engaged position illustrating how the described fiber optic terminals 18, 29 are accommodated within the connector of the present invention. While plug 14 serves to firmly hold fiber optic terminal 18 in a protruding position under hood 22, receptacle 12 serves to hold terminal 29 in a recessed position within channel 26. The matching of the channel's 26 inner diameter to the terminal's 18 outer diameter at 47 limits radial movement of the terminal 29 while coil spring 41 serves to bias terminal 29, freely moveable in an axial direction, towards the mouth of the receiving channel 26.

The electrical terminals 20, 51 employed in the connector of the present invention are also of conventional design. Each terminal consists of a strip 20, 52 of electrically conductive material. In the event the connector is to be employed to interconnect thermocouple wires, it would be necessary to form these strips of material identical to that employed in the thermocouple wires themselves as utilization of differing contact material would increase thermocouple error. It is a connector's function to bring these two strips into contact with one another in a sweeping motion in order to clear the contacting surfaces of any oxidation or other contamination that may have accumulated. Once in contact, a substantial biasing force is required to maintain an electrical interconnection.

Figure 3:
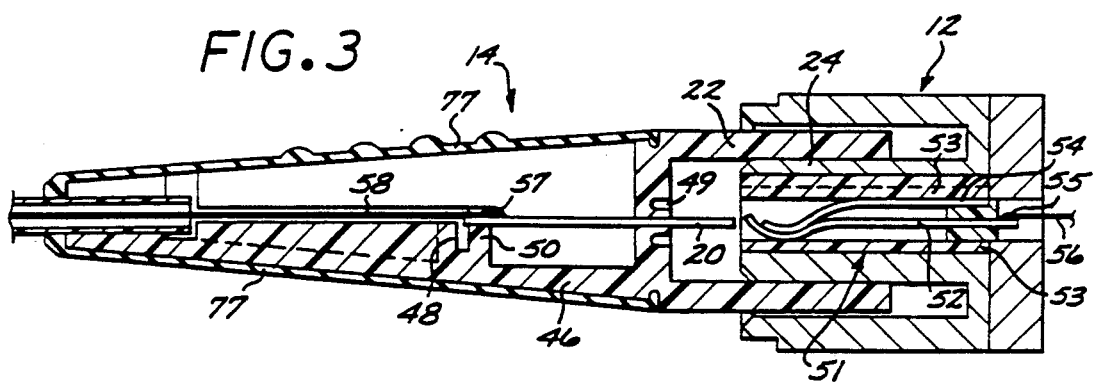
FIG. 3 is an enlarged, cross-sectional view taken along lines 3—3 of FIG. 1.

FIG. 3 is a cross-sectional view of plug 14 and receptacle 12 in a partially engaged position illustrating how the described electrical terminals 20, 51 are accommodated within the connector of the present invention. Plug 14 again serves to hold electrical terminal 20 in a protruding position within the plug's hooded section. A conductive wire 58 is attached to terminal 20 at 57, such as by soldering or welding. Receiving channel 28 of receptacle 12 accommodates a shaped strip 52 of electrically conductive material held within an insulative sleeve 53. Spring 54 biases the strip 51 towards one side of the sleeve 53 which causes the strip to firmly contact terminal 20 upon insertion. An electrically conductive wire 56 is appropriately attached to strip 52 at 55.

Figure 4:
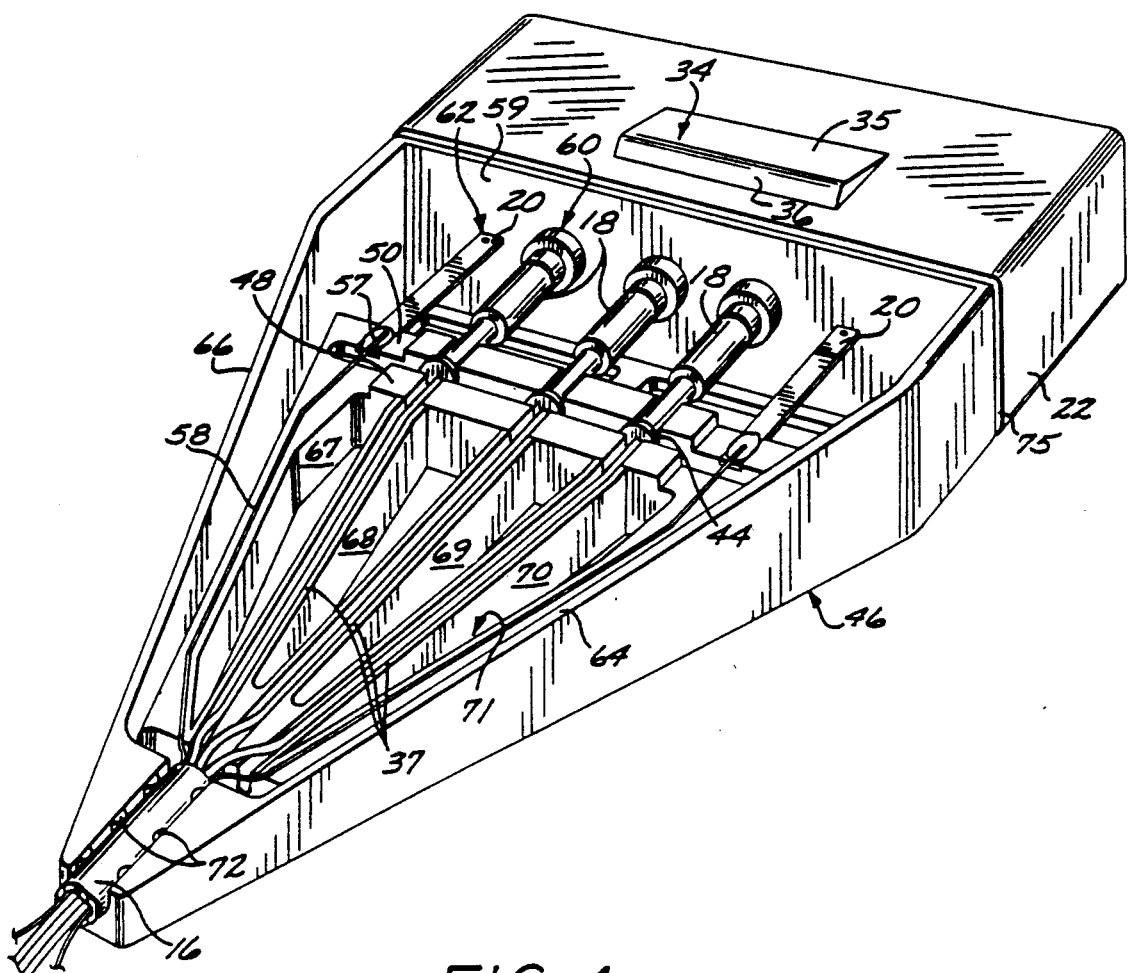
FIG. 4 is an enlarged perspective view of the connector plug of the present invention in partially assembled form.

FIG. 4 is a perspective view of plug 14 in a partially assembled state. The most prominent component visible in this illustration is armature 46 which provides a substantially rigid framework within plug 14 and extends forwardly to form hood 22. The armature 46 consists of a single molded part that includes a front wall 59 having terminal apertures 60, 62 therein, side walls 64, 66 extending backwardly to form a narrow ribbed channel 72, a pair of transverse ribs 48, 50 and a series of open faced channels 67, 68, 69, 70, 71 extending from near the ribbed channel 72 to transverse ribs 48, 50 each in alignment with one of the terminal apertures 60, 62. Apparent in FIGS. 2 and 3 are annular areas 43, 49 of decreased wall thickness centered about each terminal aperture 60, 62 on the exterior side of front wall 59.

As is visible throughout the figures, hood 22 extends forwardly well beyond front wall 59. The hood's interior wall is dimensioned to snugly fit over receptacle mound 24, while its exterior wall incorporates a wedge shaped latching mound 34 having a forwardly facing shallow tapered surface 35, and a rearwardly facing more steeply tapered surface 36. The hood 22 additionally incorporates a longitudinally oriented groove 74 on its exterior surface as visible in FIG. 1.

Armature 46 not only serves to provide a rigid framework for plug 14, but additionally aids in the assembly of the various components located therein. Additionally, armature 46 provides sufficient structural stability to the plug 14, in a partially assembled state to allow it to be fully tested prior to the final overmolding procedure. The first step in the assembly of plug 14 requires the insertion of electrical terminals 20 through the electrical terminal apertures 62. The snug fit of the terminals 20 within apertures 62 serves to hold the terminals in position. Once inserted, a bared section of electrical conduit 58 is placed on each terminal 20 at 57 where it is either soldered or welded in place. The open configuration of armature 46 permits welding electrodes to bear on each terminal blade 20 from top and bottom.

Cable 16 carries the electrical conduit 58 and optic fibers 37 and is pinched in place within ribbed channel 72. The ribs bearing down on the cable's outer jacket serve to hold the cable firmly in place. The electrical conduits are then positioned within the open faced channels 67, 71 extending from near the end of the cable's jacket toward electrodes 20 as positioned on rib 50. The optical fibers 18 which have attached thereto the previously described terminals 18 are similarly placed in their respective open faced channels 68, 69, 70 after which terminals 18 are pushed through apertures 60 and snapped into place. Each terminal 18 has a section of increased diameter 44 which is positioned between ribs 48 and 50.

The ribs 48 and 50 prevent axial movement of terminals 18, while the tight fit of electrical terminal 20 within orifice 62 precludes its longitudinal movement. As a result, the plug can be inserted into and extracted from an appropriate receptacle 12 for testing without disturbing the arrangement of components or otherwise damaging the partially assembled plug. In the event a fault is identified, it can at this point easily be rectified.

The final step in the assembly is the overmolding of the plug 14. The plug, as partially assembled, is first plugged into a receptacle which serves to firmly hold the protruding terminals 18, 19 in place. The area of decreased wall thickness 43, 49 about each terminal enables slight radial repositioning of the terminal should that be necessary to bring the terminals into proper axial alignment with the receiving channels. The plugged-in plug is then firmly held in place while a thermoplastic elastomer is molded about the entire assembly up to and about front wall 59. The openness of the armature allows the molding material to reach all surfaces of the components within the plug. The construction of cable 16 within ribbed structure 72 prevents elastomer from flowing thereinto. An elastomeric material is selected that bonds to the armature material as well as the cable's jacket. Additionally, grooves in the armature 75 provide a good mechanical interlock between the armature and the overmolding once allowed to cool. The overmolding serves to hold all components firmly in place, renders the plug substantially impervious to the influx of any contamination and resistant to shock loads.

In use, the overmolded plug, is fairly resistant to damage. Substantially impervious to the influx of any foreign matter, the plug can be sterilized while the forwardly extending hood 22 serves to protect the protruding ends of terminals 18 and 22 from potentially damaging impacts. Longitudinal groove 74 requires the plug 14 to be properly rotationally oriented prior to insertion into receptacle 12. A mismatched rotational orientation causes ridge 76 of receptacle 12 to interfere with hood 22 to effectively prevent insertion. Properly oriented, groove 74 allows the hood 22 to clear the ridge 76. In this particular embodiment the groove 74 and ridge 76 combination precludes 180° ambiguity. Once properly oriented, the inner surface of hood 22 can engage the perimeter of terminal receptacle mound 24 and causes the individual terminals 18, 20 to be guided toward the respective receiving channels 26, 28 as plug 14 is pushed into receptacle 12. Terminal 18 eventually slips into sleeve 45, engages terminal 29 and causes the coil spring 41 to be compressed as the plug 14 is fully inserted. Electrical terminal 20 slides under electrical contact 52 while the compression provided by spring 54 assures that sufficient force is applied between the contacting surfaces. Once fully inserted, latching mound 34 snaps into place within void 32. The fact that the forward face 35 of latching mound 34 has a shallower taper than the rearward face ensures that less force is required to latch than to delatch said plug 14 from receptacle 12.

While a particular form of the invention has been illustrated and described, it will also be apparent to those skilled in the art that various modifications can be made without departing from the spirit and scope of the invention. Accordingly, it is not intended that the invention be limited except as by the appended claims.

What is claimed:

1. A push-pull hybrid connector for simultaneously coupling electrical and optical conduits, comprising:

a receptacle, said receptacle having arranged therein a first set of electrical and optical terminals operatively attached to a first set of electrical and optical conduits, said receptacle having formed therein receiving channels extending from an exterior surface of said receptacle to the terminals arranged therein and further having formed therein a groove encircling said receiving channels so as to define a proximal and distal wall with respect to said receiving channels; and a plug have arranged therein and protruding therefrom a second set of electrical and optical terminals operatively attached to a second set of electrical and optical conduits, said protruding terminals being arranged so as to be receivable within said receptacle's receiving channels, said plug further having a hood extending therefrom encircling and substantially extending beyond said protruding terminals and dimensioned for receipt within said receptacle's groove, said hood having an interior surface dimensioned to be tightly received about the proximal wall of said receptacle, said hood having an exterior surface formed to enable said hood to be received within said groove only when said plug is in a preselected rotational orientation relative to the receptacle and further formed to latchingly engage said distal wall upon insertion of said plug's terminals into said receptacle's receiving channels sufficiently far to contact said receptacle's terminals.

2. The connector of claim 1 wherein said receptacle has a raised segment proximally extending from said distal wall and wherein the exterior surface of said plug's hood has formed therein a groove to enable said hood to avoid the receptacle's raised segment when in a preselected rotational orientation and allow insertion of said hood into said receptacle's groove.

3. A push-pull hybrid connector for simultaneously coupling electrical and optical conduits, such connector including a plug, having arranged therein and protruding therefrom electrical and optical terminals operatively attached to a first set of such electrical and optical conduits, such connector further including a receptacle, having arranged therein electrical and optical terminals operatively attached to a second set of electrical and optical conduits, said receptacle having formed therein receiving channels for receiving the protruding portion of the plug's terminals to enable contact with the receptacle's terminals and further having formed therein a deep groove encircling said receiving channels to define a proximal and distal wall with respect to said receiving channels, said plug further comprising:

a hood extending from said plug encircling and substantially extending beyond said protruding terminals and dimensioned for receipt within said receptacle's groove, said hood having an interior surface dimensioned to be tightly received about the proximal wall of said receptacle, said hood having an exterior surface formed to enable said hood to be received within said groove only when said plug is in a preselected rotational orientation relative to the receptacle and further formed to latchingly engage said distal wall when said plug's terminals are in contact with said receptacle's terminals.

4. The connector of claim 3 wherein said receptacle has a void formed in its distal wall, wherein said plug's hood is formed of slightly resilient material and wherein a raised mound is formed on said hood's exterior surface, dimensioned and positioned to snap into the void of the receptacle's distal wall when said plug is in a fully inserted position within said receptacle.

5. The connector of claim 4 wherein said raised mound has a forward facing surface and a rearward facing surface and wherein said forward facing surface rises above the hood's exterior surface at a shallower angle than the angle at which the rearward facing surface rises above the exterior surface.

6. The connector plug of claim 5 further comprising an overmolding substantially encapsulating said rigid molding having positioned therein said cable's jacket, said conduits and said electrical and optical terminals.

7. A hybrid connector plug for simultaneously coupling electrical and optical conduits contained within a jacketed cable to a receptacle having positioned therein electrical and optical terminals, comprising:

a single piece, substantially rigid molding to aid in the assembly of said plug and ultimately to be substantially incorporated within said plug, said molding including an apertured front wall and further formed to releasably grasp an end of said cable's jacket, guide electrical and optical conduits extending from within said cable towards said front wall and to enable electrical and optical terminals, operatively affixed to said conduits, to be removably positioned so as to protrude through said apertures of said front wall.

* * * * *